United States Patent [19]

Russell et al.

[11] Patent Number: 5,739,237

[45] Date of Patent: Apr. 14, 1998

[54] MATERIALS AND THEIR USE IN THE PREPARATION OF BIOCOMPATIBLE SURFACES

[75] Inventors: Jeremy Colin Russell; Ewan James Campbell, both of Surrey, United Kingdom

[73] Assignee: Biocompatibles Limited, Surrey, United Kingdom

[21] Appl. No.: 682,536

[22] PCT Filed: Jan. 27, 1995

[86] PCT No.: PCT/GB95/00161

§ 371 Date: Jul. 29, 1996

§ 102(e) Date: Jul. 29, 1996

[87] PCT Pub. No.: WO95/20407

PCT Pub. Date: Aug. 3, 1995

[30] Foreign Application Priority Data

Jan. 28, 1994 [WO] WIPO ............... PCT/GB94/00177
Aug. 4, 1994 [GB] United Kingdom ............... 9415926

[51] Int. Cl.[6] ............... C08F 30/02; C08F 20/58; C08F 20/60; C07F 9/06; C07F 9/22; C07F 9/28
[52] U.S. Cl. ............... 526/277; 526/307.7; 526/289; 558/166; 558/199; 558/214
[58] Field of Search ............... 526/277, 307.7, 526/289; 558/166, 199, 214

[56] References Cited

U.S. PATENT DOCUMENTS 5,422,402  6/1995  Bowers et al. ............... 525/328.2

FOREIGN PATENT DOCUMENTS

| | | | |
|---|---|---|---|
| 0 032 622 | 7/1981 | European Pat. Off. | C07F 9/10 |
| 0 157 469 | 10/1985 | European Pat. Off. | C07F 9/10 |
| 0 537 972 A1 | 4/1993 | European Pat. Off. | G02B 1/04 |
| WO 86/02933 | 5/1986 | WIPO | C08G 18/38 |
| WO 87/02684 | 5/1987 | WIPO | C08K 5/00 |
| WO 88/00956 | 2/1988 | WIPO | C08G 63/68 |
| WO 91/06020 | 5/1991 | WIPO | G02B 1/04 |
| WO 91/13639 | 9/1991 | WIPO | A61L 33/00 |
| WO 92/06719 | 4/1992 | WIPO | A61L 33/00 |
| WO 92/07858 | 5/1992 | WIPO | C07F 9/09 |
| WO 92/07885 | 5/1992 | WIPO | C08F 212/14 |
| WO 92/21386 | 12/1992 | WIPO | A61L 33/00 |
| WO 93/01221 | 1/1993 | WIPO | C08F 246/00 |
| WO 93/05081 | 3/1993 | WIPO | C08F 8/40 |
| WO 93/15775 | 8/1993 | WIPO | A61L 33/00 |
| WO 94/16748 | 8/1994 | WIPO | A61L 33/00 |
| WO 94/16749 | 8/1994 | WIPO | A61L 33/00 |

OTHER PUBLICATIONS

Pharmazie, 1979, vol. 34, H.12, pp. 345 (with English Translation of the Abstract.).

J. Amer. Soc. Artifical Internal Organs, 1994, vol. 40, No. 3, pp. 001–005, E.J. Campbell et al.

Blood, 1991, vol. 78, No. 3, pp. 673–680, R.A. Sheppeck et al.

P. Kertscher, H.-J. Ruger and P. Nuhn, Pharmazie 34, H. 12, 1979, p. 5.

*Primary Examiner*—Joseph L. Schofer
*Assistant Examiner*—Wu C. Cheng
*Attorney, Agent, or Firm*—Sughrue, Mion, Zinn, Macpeak & Seas, PLLC

[57] ABSTRACT

New materials having improved biocompatibility have novel zwitterionic groups at the surface. The zwitterion is characterized by having at least one monovalent substituent at the atom carrying the cationic charge which is an aryl group. Preferably the atom carries at least two, and preferably three such aryl, usually phenyl, groups. The cationic group is preferably a triphenylphosphonium. Treatment of surfaces to provide pendant zwitterionic groups of the specified type have reduced platelet activation, whilst they do not appear to reduce platelet adhesion. The invention has utility in the field of blood contacting device, especially devices for implantation, such as vascular grafts.

39 Claims, No Drawings

MATERIALS AND THEIR USE IN THE PREPARATION OF BIOCOMPATIBLE SURFACES

The present invention relates to new materials having improved biocompatibility and may be applied to or form a surface having improved biocompatibility. The materials have novel zwitterionic groups which are found to be less thrombogenic than existing materials, though having relatively high levels of platelet adhesion.

Materials used in medical devices where cell growth on the surface is desired, for example in cardiovascular stents and vascular grafts ideally must allow for the ready attachment of endothelial cells. As the mechanism of cell attachment and platelet adhesion are similar, it would be ideal if such a material did not activate platelets. Thus platelet adhesion without platelet activation would be a suitable combination of properties to ensure that thrombus formation does not occur, but endothelial cell growth is supported. With such a combination of properties, new devices which are currently impractical, such as small diameter vascular grafts, will become feasible.

It is known to reduce platelet activation by mimicking the surface of a red blood cell by coating a surface with phosphoryl choline zwitterionic groups. Various ways of introducing such groups at the surfaces of substrates are described in our earlier patent publications EP-A-0032622, EP-A-0157469, WO-A-9207858, WO-A-9113639, WO-A-9301221 and WO-A-9315775 and WO-A-9207885. In WO-A-9416748 (unpublished at the priority date of the present invention) various types of zwitterionic groups other than phosphoryl choline groups are described. For instance the trimethylammonium cation is replaced by various groups, including pyridinium groups. In other types of compound described in that document, the chain joining a phosphate ester and a quaternary nitrogen atom is increased in length or is an arylene group including heteroarylene. Further zwitterionic groups are also described in our earlier patent publication WO-A-9416749 (which was not published at the priority date of the present invention). One exemplified compound disclosed in WO-A-9416748 has a triphenylphosphonium group as the cation of the zwitterion (the priority date for that specific compound is the same as in the present application). The present inventors have discovered that the triphenylphosphonium derivative appears to provide reduced platelet activation, but without reducing platelet adhesion. This is thought to be a result of the cation having at least one aryl group as a monovalent substituent and the present invention is based on that discovery.

In the present invention there is provided a surface having pendant zwitterionic groups in which the atom carrying the cationic charge has at least one monofunctional (or monovalent) (that is one of the substituents at that atom other than the substituent which joins the atoms to the anionic group and/or the surface) substituent which is an aryl, heteroaryl or aralkyl group.

In the invention the pendant zwitterionic groups can be represented by the formula (I)

—YWZ, (I)

in which one of Y and Z is a cationic moiety having the defined aryl substituent, and the other of Y and Z is an anionic moiety and in which W is an alkylene (including cycloalkylene and cycloalkyl alkylene), arylene, heteroarylene and alkarylene, in which any alkylene chain, including cycloalkylene, may be interrupted by one or more oxygen atoms, and any of which groups may be unsubstituted or substituted by nonionic non-interfering substituents.

Preferably the cationic moiety is positioned further from the surface than the anionic moiety, that is Z represents the cationic moiety.

Preferably the zwitterionic group has the formula II:

in which B is a divalent anionic moiety,

W is as defined above,

A is a nitrogen atom, a phosphorus atom or a sulphur atom, n is 1 when A is sulphur and n is 2 when A is nitrogen or phosphorus, R is an aryl, heteroaryl or alkaryl group preferably aryl, usually phenyl.

and the or each $R^1$ is independently selected from aryl, heteroaryl, aralkyl and alkyl groups and hydrogen atoms. Preferably each $R^1$ is other than a hydrogen atom more preferably each is aryl, usually phenyl.

Preferably the group W separates the anionic and cationic moieties by a chain including at least 2 carbon atoms, preferably at least 5 carbon atoms and up to 20, more preferably up to 10 carbon atoms. The group W therefore preferably includes an alkylene group comprising at least 6, for instance at least 7, carbon atoms separating the ionic moieties. The group W is, preferably, alkylene of 5 or more, preferably at least 6, for instance at least 7 carbon atoms optionally containing one or more ethylenically unsaturated double or triple bonds or oxygen atoms, arylene, alkarylene, aralkylene, alkylene aralkylene, cycloalkylene, alkylene cycloalkylene, cycloalkylalkylene or alkylene cycloalkylene, most preferably alkylene, optionally containing one or more fluorine substituents and/or one or more functional groups.

Preferably the group B in the general formula II is III:

in which $X^1$ and $X^2$ are independently selected from a bond, —O—, —NH— and —S—. The group B is thus a phosphate ester group or a phosphate ester group in which one or both the oxygen atoms is replaced. Preferably the group B is a phosphate ester group, that is a group in which both $X^1$ and $X^2$ are oxygen atoms.

The group —YWZ may be part of a conjugated di-yne of the general formula VI:

in which at least one of $R^3$ and $R^4$ is an acyl residue of a fatty acid having a conjugated di-yne group. Preferably both $R^3$ and $R^4$ are such groups and are preferably the same. Where only one of $R^3$ and $R^4$ is comprises a conjugated di-yne, the other is preferably a $C_{1-24}$, preferably $C_{8-20}$ alkyl group. The groups $R^3$ and $R^4$ are suitably represented by the groups $B_2$ and $B_3$, respectively, specified in our earlier patent publication EP-A-0,032,622, the content of which is incorporated herein by reference. In particular the novel surface of the present invention may be provided by coating a surface with compounds of the formula VI and, preferably, subsequently polymerising the compound in situ to form a crosslinked polymer containing repeat units analogous to those specified in EP-A-0,032,622.

Alternatively the group —YWZ may be part of a glyceride having the formula VI in which $R^3$ and $R^4$ each represent $C_{8-24}$ alkyl or alkanoyl groups, in which the alkyl groups are usually straight chain alkyl. Such compounds may be coated onto hydrophobic substrate surfaces and retained by physisorption. Such methods are described in our copending application, no. WO-A-92/06719, the content of which is incorporated herein by reference.

Alternatively the zwitterionic group at the surface may be provided by coating and reacting the surface with a compound of the formula IV:

$$R^2—Y—W—Z \qquad \qquad IV$$

in which $R^2$ represents a group which reacts with or adsorbs onto the surface or reacts with a substrate polymer which can be coated onto the surface or which can polymerise or is a polymer residue. The substrate generally comprises a polymer material, so that a reactive group $R^2$ includes a group which reacts with moieties on the substrate surface. The group at the polymer surface which reacts with the compound of the formula IV is generally a hydroxyl group, an amine group or a carboxylic acid group (—COOH). Where the polymer substrate has no such groups, it may be activated in an initial step, by known etching or derivatising techniques such as grafting, which introduce hydroxyl, carboxylic or primary or secondary amino groups on the surface (see for example "Chemical Reactions of Polymers", Ed E M Fettes (1964), Interscience Publishers, London). Suitable reactive groups as $R^2$ are described in our earlier patent publications nos. WO-A-91/06020, WO-A-91/13639, WO-A-92/07858, EP-A-0,157,469 and WO-A-93/05081, the contents of which are herein incorporated by reference. Particularly preferred reactive groups are activated amine groups such as are described in WO-A-9207858 and moieties which have the leaving groups discussed in WO-A-9113639.

The zwitterionic group may, as an alternative to being attached to the surface using a relatively small, low molecular weight reagent such as such classes of compound of the formula IV, be applied to a substrate as a coating material including a polymeric compound having pendant zwitterionic groups. A polymer having zwitterionic pendant groups may, for instance, comprise residues of a polymerisable compound containing a zwitterionic group YWZ. The polymer may be a homopolymer or copolymer of a polymerisable compound containing the zwitterionic group. Alternatively a polymeric compound containing such groups may be a polymer onto which the zwitterionic groups YWZ have been reacted, for instance using reactive groups of the type specified for $R^2$ above.

Such polymers may, for example, be condensation polymers such as polyesters, polyurethanes or polymers of ethylenically unsaturated compounds, such as polyolefins, poly(alk)acrylates, for examples polyacrylates or polymethacrylates, polystyrenes or polyvinyl polymers.

Specific examples of polymers containing zwitterionic groups used in the present invention are polyurethanes, for instance as described in our earlier patent publication no. WO-A-86/02933, polyesters such as described in our earlier patent publication WO-A-88/00956 or, preferably, acrylate polymers such as described in WO-A-93/01221, the content of which are all incorporated herein by reference. Coating of substrates with grafted polymers is described in our earlier application WO-A-93/15775, which describes also reaction of zwitterionic groups onto preformed polymers, especially naturally derived polymers or derivatives thereof, such as cellulosic polymers, and the content of that specification is incorporated herein by reference. Other polymers onto which zwitterionic groups have been reacted by the free radical graft polymerisation of an ethylenically unsaturated compound containing zwitterionic groups, is described in our earlier application no. WO-A-93/05081, the content of which is incorporated herein by reference.

As an alternative to providing the pendant zwitterionic groups at the surface by coating a preformed substrate, as described above, the zwitterionic groups may be present in the bulk of the material forming the substrate. The zwitterionic group may be present as a moiety of a lipid-like plasticiser molecule, for instance analogous to the products described in our earlier application no. WO-A-87/02684, the content of which is incorporated herein by reference. Alternatively the zwitterionic group may be a pendant group of a polymer. The polymer may be a polyurethane or a polyester, of the same type, though solid, as those described above as suitable for providing coatings. Preferably the polymer is formed from ethylenically unsaturated polymerisable compounds, such as polyolefins or, preferably, poly(alk) acrylates. Such polymers are described in our earlier patent publication no. WO-A-92/07885, the content of which is incorporated herein by reference. Such polymers may, for instance, comprise the residues of one or more diluent copolymerisable comonomers. The polymers may, further, be crosslinked, by incorporation of polyfunctional ethylenically unsaturated monomers which become incorporated into the polymer chains upon free radical polymerisation.

The surface of the present invention may comprise pendant groups of the formula IV in which $R^2$ has the formula VII

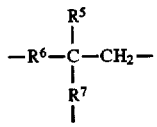

in which $R^5$ is hydrogen, alkyl of 1–12 carbon atoms, preferably 1–4 carbon atoms, which is unsubstituted or substituted by a group capable of reacting with a hydroxyl, amino or carboxyl group, or with a biologically active compound, or $R^5$ is a polymerisable, preferably ethylenically unsaturated group, $R^6$ and $R^7$ are the same or different and are each selected from methylene or carbonyl groups, and through at least one of which the zwitterionic group is bound to the surface.

Preferably each of $R^6$ and $R^7$ is methylene, and is preferably bound to an oxygen atom.

The present invention provides further novel compounds of the formula IV in which $R^2$ is a moiety of the formula VII, in which $R^6$ and $R^7$ are identical and are attached to identical groups, especially groups of the formula VIII

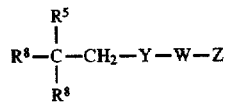

in which the groups $R^8$ are selected from the group ($R^2$—Y—B'—) defined in WO-A-9416748, wherein B' is —CH$_2$— or —C(=O).

Preferably each $R^8$ represents $R^9$—E—B'— where B' is as defined earlier and where E is a valence bond or a linking group selected from —O—, —S—, —NH—, —OC(O)—, —C(O)—O—, —SC(O)—, —C(O)—S—, —NHC(O)—, —C(O)—NH—, —OC(O)O—, —SC(O)O—, —NHC(O)O—, —OC(O)S—, —SC(O)S—, —NHC(O)S—, —OC(O)NH—, —SC(O)NH— and —NHC(O)NH— and $R^9$ is hydrogen, alkyl, alkenyl or alkynyl of up to 25 carbon atoms, optionally containing one or more etheric oxygen atoms and unsubstituted or substituted by one or more fluorine atoms and/or functional groups capable of reacting to provide covalent attachment to a surface and/or polymerisable groups.

Most preferably E is —O— and $R^9$ is a linear $C_{8-24}$ alkyl group or linear $C_{8-24}$ alkanoyl group.

The zwitterionic group may be a moiety on an analogue of a phospholipid, especially a fatty acid diester or diether of the formula VI, in which $R^3$ and $R^4$ represent saturated and unsaturated ester or ether residues derived from fatty acids or is a diester or diether of the formula VIII in which the groups $R^8$ represent saturated or unsaturated ester or ether residues derived from fatty acids. Preferably the fatty acid residues are straight chain and contain from 12-20 carbon atoms. Such compounds may be used to coat hydrophobic substrates such as PVC, polyethylene or polypropylene by application of a solution in an organic solvent, followed by drying, as described in our co-pending application no. WO-A-92/06719, the content of which is incorporated herein by reference. Alternatively the phospholipid analogue may be incorporated by blending with a polymer compound, especially a thermoplastic polymer, when it behaves a simple external plasticiser, as described in our co-pending application no. WO-A-87/02684, the content of which is incorporated herein by reference.

Phospholipid analogues of the formula VI in which $R^3$ and $R^4$ represent saturated or unsaturated acyl or alkyl groups, especially $C_{12-20}$ straight chain alkyl are novel compounds.

The present invention provides also novel compounds of the formula IV, in the which the group $R^2$ represents a moiety having a reactive group capable of reacting with hydroxyl, amine or carboxylic acid groups. Such compounds are described above as reactants for derivatising a substrate surface.

The present invention provides also novel compounds of the formula IV in which the group $R^2$ is a polymerisable group. The group $R^2$ may be a difunctional moiety capable of reacting in a condensation polymerisation process, for instance to form a polyurethane, polyester or polyamide. The functionalities may be selected from carboxylic acid, hydroxyl, amino or isocyanate. Alternatively the polymerisable moiety $R^2$ may comprise a free radical polymerisable ethylenically unsaturated group, preferably a styrene, vinyl or (alk)acrylate moiety. Such compounds may be used to form addition homo or copolymers, as described above. Alternatively the ethylenically unsaturated moiety of $R^2$ may be graft polymerised onto a substrate to form the surface having zwitterionic groups. A particularly preferred class of compounds has the general formula IX:

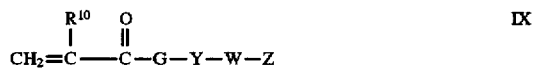

in which $R^{10}$ is hydrogen or $C_{1-4}$ alkyl, preferably methyl, and G is —O—$R^{12}$ or —N($R^{11}$)—$R^{12}$— in which $R^{11}$ is hydrogen, $C_{1-4}$ alkyl or $R^{12}$—Y—W—Z and $R^{12}$ is $C_{1-12}$ alkylene, preferably $C_{2-6}$ alkylene.

The present invention provides polymers, including homo and copolymers, of any such polymerisable compounds. An especially preferred class of polymer compounds comprises copolymers with copolymerisable monomer which provides a pendant group capable of providing stable binding of the copolymer to a surface. The binding may be by covalent bond formed after coating of the preformed copolymer on to the surface, or by counter ionic bonding between oppositely charged groups on the polymer and on the surface. Preferably the bonding is by hydrophobic interaction between a non polar, usually $C_{8-24}$ alkyl chain on the polymer and a hydrophobic surface. Especially preferred copolymers are of the zwitterionic (alk)acrylate monomer of the formula IX above and $C_{8-20}$-alkyl (alk)acrylate monomer.

The present invention comprises especially novel compounds of any of the above classes in which the group W separates the anionic and cationic moieties by a chain including at least 2 carbon atoms, preferably at least 5 carbon atoms and up to 20, more preferably up to 10 carbon atoms. The group W therefore preferably includes an alkylene group comprising at least 6, for instance at least 7 carbon atoms separating the ionic moieties. The group W is, preferably, alkylene of 5 or more, preferably at least 6, for instance at least 7 carbon atoms optionally containing one or more ethylenically unsaturated double or triple bonds or oxygen atoms, arylene, alkarylene, aralkylene, alkylene aralkylene, cycloalkylene, alkylene cycloalkylene, cycloalkylalkylene or alkylene cycloalkylene, most preferably alkylene, optionally containing one or more fluorine substituents and/or one or more functional groups.

The invention provides further the use of compounds containing zwitterionic groups —YWZ in improving the biocompatibility and/or hydrophilicity (including lubricity) of a surface. It relates to a method of improving the biocompatibility and/or hydrophilicity of a surface by providing a surface having such pendant zwitterionic groups.

In the new use, a substrate is coated with a composition comprising a compound having a zwitterionic group —YWZ, so as to provide a surface having pendant zwitterionic groups YWZ. In the method the properties of the substrate are improved by reducing platelet activation, whilst platelet adhesion is substantially unaffected. Platelet adhesion may be increased or may be reduced to a small extent, for instance by less than 50%, more preferably by less than 20% or less than 10%. The tests for platelet adhesion and activation are described below. The platelet activation is preferably reduced by the method of the invention by at least 50%, preferably by at least 75%, by the provision of zwitterionic groups.

An alternative test for determining the effectiveness of the method of the present invention in reducing platelet activation is the determination of Factor XII activation. The test is described by E J Campbell, V O'Byrne, P W Stratford, I H Quirk, T A Vick, M C Wiles, and Y P Yianni in "Biocompatibles Studies using Methacrylolylphosphorylcholine Lauryl Methacrylate Copolymer", J Amer. Soc. Artificial Internal Organs, 1994, vol 40, No. 3, pM853-M857 and described below. The method of the present invention preferably reduces activated Factor XII in plasma by at least 50%, preferably at least 75% and sometimes as much as 90%, as compared to the amount of activated Factor XII produced in the presence of the untreated substrate. This test demonstrates the properties of the zwitterionic groups in reducing contact activation, a component of the intrinsic pathway of the coagulation cascade.

Substrates treated by the method of the present invention, as well as components having the specified surfaces may be used in a range of products where it is desired that cells are attached to the surface but thrombosis does not occur. The products are therefore preferably used in a blood or blood cell containing environments, especially on devices to be inserted, especially implanted, in the human or animal body, especially those implanted for an extended period of time, especially a week or more, for instance permanently. The invention is of particular value for vascular grafts and cardiovascular stents, especially relatively small diameter components of those types, or for wound-treatment products, where it is desired for epithelial or other anchorage-dependent cells to grow.

The present invention is illustrated in the accompanying examples:

TEST METHODS

Platelet Activation Test

Blood was collected from a healthy adult volunteer using the double syringe method where the first 5 ml of blood is discarded. The blood was collected into trisodium citrate (32 g/l) in the proportion of 9 volumes to 1 volume citrate in plastic tubes. The samples were kept at room temperature on a spiral mixer until used.

Samples of polyethylene ribbon were treated with sample compound as described below and untreated polyethylene ribbon were used as controls.

Half of the test samples were incubated with citrated blood (200 μl) and the remainder were incubated with EDTA-treated blood on a phase shaker for 30 minutes before washing in PBS four times. Platelet adhesion was measured in a manner similar to that described above for fibrinogen that is using enzyme immunoassay, using monoclonal antibodies to GPIb (cf Sheppeck R A et al. Blood (1991) 78:673–680). Platelet activation was measured in a manner similar to that described above for detection of proteins by enzyme immunoassay using monoclonal antibodies against P-selectin (GMP140) to detect the presence of this platelet activation marker on the surface of biomaterials. In the presence of EDTA, which extracts calcium from inside platelets, activation is inhibited, so that incubation with EDTA-treated blood acts as a non-specific control for activation, obviating the need for incubation in non-specific antibody.

Fibrinogen Adsorption

The assay determines adsorption of human fibrinogen at a surface. This protein is representative of protein which is typically adsorbed at a surface. The assay can be readily modified to determine the adsorption of other proteins.

Polyethylene tubing was coated with a sample and human plasma (5 ml) was pumped through the tubing using a Watson-Marlow multi-head peristaltic pump (lowest setting). The tubing was then washed by pumping through phosphate buffered saline (PBS) (×2). A solution containing antibodies specific to human fibrinogen (5 ml) was then pumped through followed by a further wash of PBS (×2). A conjugate of horseradish peroxidase and a second antibody specific to the first fibrinogen-specific antibody (5 ml) was passed through followed by a further wash of PBS (×2). o-Phenylenediamine in phosphate-citrate buffer (5 ml), (0.8 mg/ml) was passed through and the absorption at 450 nm was read using a microplate reader.

Results are calculated as the percentage reduction in absorption at 450 nm compared to an untreated sample of polyethylene tubing. As a control for non-specific binding of antibody to the samples each sample was also incubated with non-specific antibody.

Platelet Adhesion by Scanning Electron Microscopy

Samples were incubated in citrated blood, (9:1 32 g/L), for 30 minutes at ambient temperature. Samples were then washed in phosphate buffered saline (PBS) and fixed with 2% glutaraldehyde in PBS for 15 minutes. Samples were then dehydrated using serial dilutions of alcohol (50–100%) and air dried. Samples were sputtered with gold and scanned in a S100 Scanning electron microscope. The micrographs show the presence and shape of platelets. From the characteristics shapes of activated and non-activated platelets, the extent of activation, if any, can be determined.

Factor XII Contact Activation Test

Contact activation of citrated fresh frozen plasma (FFP) by a compound under test onto a surface was determined using a commercially available activated Factor XII (FXIIa) kit produced by Shield Diagnostics (Dundee, Scotland). 7 mm×7 mm square samples of material were incubated in 250 μl FFP, in a haemocompatible material coated microtiter plate, for 60 min. 100 μl samples from each test well then were added to the precoated assay wells and incubated at ambient temperature for 60 min. Plasma samples were decanted and well washed four times using borate buffer. One hundred microliters Shield sheep anti-human FXIIa alkaline phosphatase labelled conjugate, in Tris buffer with a protein stabiliser, then was added to each test well. The plate was then incubated at ambient temperature for 60 mns and again washed 4 times with borate buffer and the plate blotted. One hundred microliters phenolphthalein monophosphate (PMP) solution, with $Mg^{2+}$ enzyme cofactor, was added to each well and incubated for 10 min. Finally 100 μl sodium hydroxide/ethylenediaminetetraacetic acid (EDTA) in carbonate buffer (pH>10) was added to stop the reaction. The wells were read in a microplate reader at 550 nm, and absorbances compated with standard solutions of FXIIa supplied to calculate the amount of activated FXII present. The background level of plasma FXIIa was subtracted from these results to determine activation caused by the surface.

EXAMPLE 1

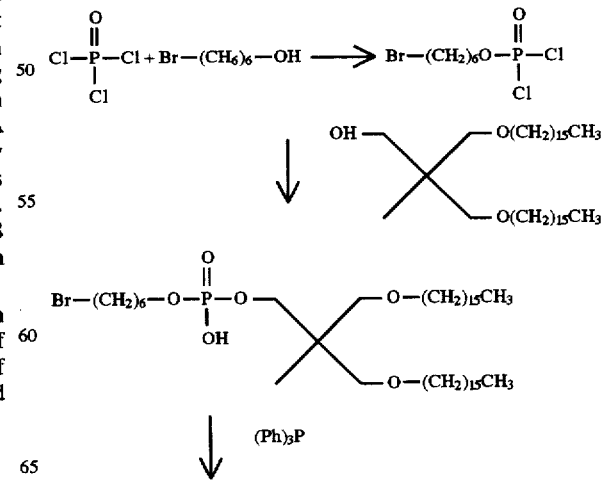

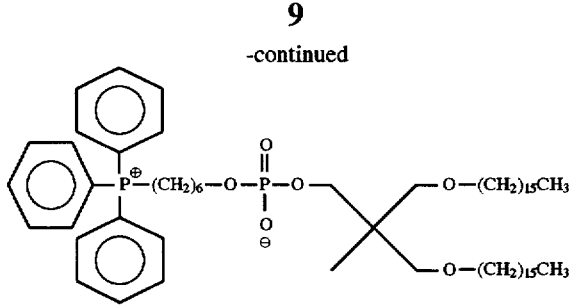

6-Bromohexan-1-ol was added dropwise to phosphorusoxy chloride (equimolar) in dichloromethane over 30 minutes under nitrogen. The mixture was stirred at room temperature under nitrogen for 16 hours. The mixture was evaporated, dried under vacuum, then distilled under vacuum, to give the pure 6-bromohexyldichlorophosphate compound. Triethylamine and dichlorophosphate (equimolar) were added dropwise over 2 minutes under nitrogen to 1,3-dihexadecyloxy-2-(hydroxymethyl)-2-methyl propane (0.3×molar amount of dichlorophosphate) in dry diethyl ether. The mixture was heated at 60° C. under nitrogen for 16 hours before triethylamine (same molar amount as dichlorophosphate) and water were added and heating maintained for a further two hours. After cooling, the aqueous layer was removed and the residue evaporated to dryness and azeotroped with benzene (×3). The residue was dissolved in diethylether, filtered and evaporated to give a crude product, which was at least partially purified by silica gel chromatography using chloroform:methanol:25% ammonia (690:270:64). Triphenylphosphine was added to the intermediate thus prepared in dry chloroform. The mixture was heated at 60° C. for 16 hours before it was cooled and the solvents evaporated under reduced pressure. The residue was purified by silica gel chromatography, elusing with chloroform:methanol (3:1) to chloroform:methanol:water (65:25:4). Fractions containing the desired compound were combined and evaporated under reduced pressure to give the desired final compound.

The compound was coated onto polyethylene strips from an ethanolic solution of 5 mg/ml. The coated strips were tested for fibrinogen adsorption. This test is generally used to indicate haemocompatibility. Normally, high fibrinogen binding indicates high platelet adhesion and subsequent activation and thus poor haemocompatibility. The results of the test, that is of adsorbence at 450 nm was, for the uncoated polyethylene, 0.494 and, for the polyethylene coated with the triphenylphosphonium compound, 0.385. Both coated and uncoated polyethylene thus gave relatively high levels of fibrinogen adsorption.

The polyethylene coated with the triphenylphosphonium compound was assayed for platelet adhesion using an anti-GPIb antibody and platelet activation using an anti-P-selectin antibody. In these experiments, although both the uncoated and coated polyethylene showed high levels of platelet adhesion, the coated material did not show the high level of platelet activation normally associated with this level of adhesion.

The results of the tests are as follows:

|  | Uncoated Plt. adhesion | Uncoated Plt. activation | Coated Plt. adhesion | Coated Plt. activation |
|---|---|---|---|---|
| Abs., 450 nm | 0.479 | 0.550 | 0.456 | 0.125 |

The coated and uncoated samples were also subjected to the S.E.M. test for platelet adhesion. The micrographs of the coated sample reveal adhered platelets (as do the uncoated controls), though the the platelets adhered to coated samples show less activation than those on the uncoated controls.

Thus the triphenylphosphonium compound provides a material which allows platelet adhesion without concomitant activation.

The amount of activated Factor XII (FXIIa) in plasma incubated with polyethylene or coated polyethylene was determined using the test described by Campbell et al (op. it.). The level of FXIIa in plasma is indicative of the extent to which the contact activation of the coagulation cascade has been activated. The results are as follows:

|  | Uncoated | Coated |
|---|---|---|
| ng/ml Factor XII above plasma level | 3.804 | 0.359 |

The results of the Factor XIIa assay clearly demonstrate that the coated material is superior to the uncoated polyethylene in that it causes reduced activation of the coagulation cascade.

EXAMPLE 2

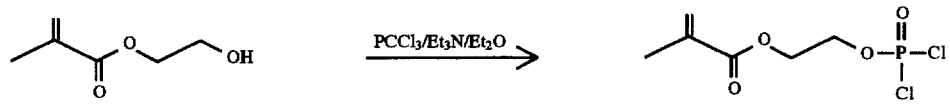

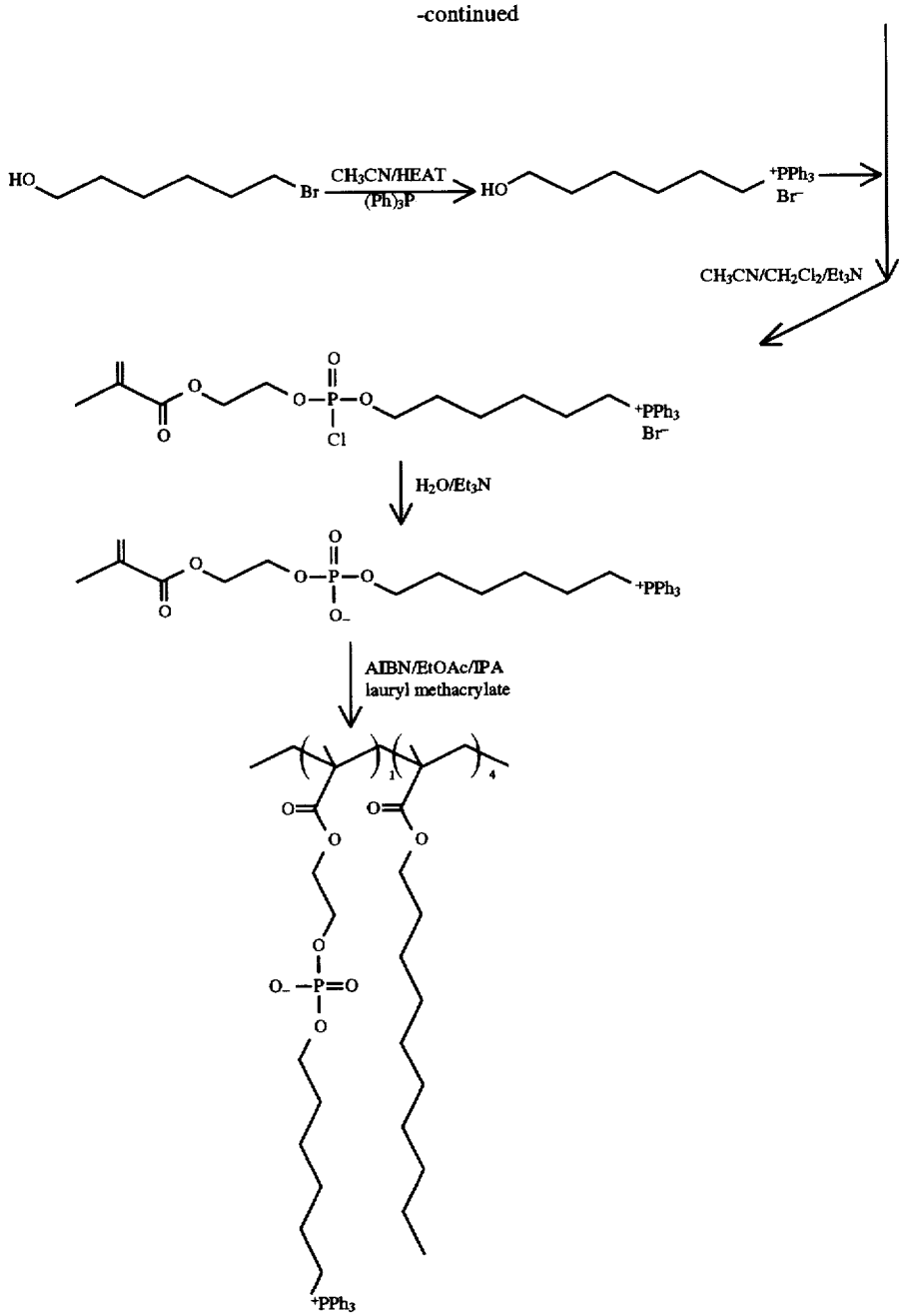

To 6-bromohexan-1-ol (10 g) in dry acetonitrile (200 ml) was added triphenylphosphine (14.5 g) and the mixture was heated in a sealed vessel at 70° C. for 64 hours. The solvent was evaporated to dryness and the residue was dissolved in chloroform (150 ml) and added dropwise to stirred diethylether (500 ml). The solid was allowed to settle and the supernatant was decanted and the residue washed with diethylether (100 ml) and dried under vacuum over phosphorus pentoxide. The solid was dissolved in dichloromethane (200 ml) and subjected to Dean-Stark drying conditions at 70° C. for six hours. The dried solution of hydroxyhexyltriphenylphosphonium bromide was kept until needed.

To a cooled (−10° C.) solution of phosphorus oxychloride (6.20 g) in dry diethylether (60 ml) was added, dropwise, a mixture of 2-hydroxyethylmethacrylate (HEMA, 5.34 g) and triethylamine (4.15 g) in diethylether (40 ml). The mixture was allowed to warm to room temperature and stirred for two hours. The solution was filtered and the filter bed washed with diethylether (30 ml). The combined solution and washings were evaporated and the residue dissolved in acetonitrile (40 ml) and added to the solution of hydroxyhexyltriphenylphosphonium bromide together with triethylamine (4.15 g) and stirred at room temperature for 16 hours.

Water (10 ml) and triethylamine (4.15 g) was added and stirring maintained for a further two hours. The solvent was evaporated, further water (30 ml) was added and the solution was washed with a mixture of ethyl acetate and diethylether (1:1, 100 ml). The aqueous layer was evaporated to dryness and azeotroped with benzene (×3) to give a residue that was purified by silica gel chromatography (×2) under a slight positive pressure, eluting with chloroform:methanol (9:1). Those fractions containing product were combined and evaporated to give a residue that was dissolved in chloroform (10 ml) and washed with water (10 ml). The organic layer was evaporated to give the monomer, 720 mg.

$^1$H-nmr (200 MHz,CDCl$_3$), 1.40–1.80 (8H,m), 1.95 (3H, s), 3.65 (2H,m), 3.95 (2H,m), 4.10 (2H,m), 4.30 (2H,m) 5.50 (1H,s), 6.10 (1H,s), 7.60–7.90 (15H,m)

Monomer (320 g) was dissolved in isopropyl alcohol (11.5 ml) and lauryl methacrylate (2.53 g) in ethyl acetate (3 ml) was added. The mixture was heated under a constant flow of nitrogen for 24 hours at 65° C. after adding α-azoisobutyronitrile (4 mg in ethyl acetate) (1 ml). The solvents were evaporated and the residue was redissolved in methanol (5 ml) and dripped into hexane (100 ml). The resulting solid was filtered off and the solvents were evaporated. The residue was titrated with hexane (×3), centrifuging the mixture between each wash. The resulting pellet was dissolved in a mixture of methanol and water (1:1, 30 ml), which was then evaporated to remove most of the methanol to leave a white aqueous suspension, which was filtered and dried to give the desired product, 100 mg.

$^1$H-nmr (200 MHz, CDCl$_3$/CD$_3$OD), 0.8–2.0 (173H,m), 3.0–4.3 (20H, m), 7.6–8.0 (15H,m)

Gel permeation chromatograhy indicated an average molecular weight of 580000 when compared to polymethyl methacrylate standards.

The polymer was coated onto polyethylene strips from a 3 mg/ml ethanolic solution. The coated strips were tested for fibrinogen adsorption. The results of the test, that is of absorbence at 450 nm was, for the uncoated polyethylene 0.898 and, for the polyethylene coated with triphenylphophonium compound, 0.600. Both coated and uncoated polyethylene thus gave relatively high levels of fibrinogen adsorption.

The polyethylene coated with the triphenylphosphonium polymer was assayed for platelet adhesion using an anti-GPIb antibody and platelet activation using an anti-P-selectin antibody. In these experiments, although both the coated and uncoated polyethylene showed high levels of platelet adhesion, the coated material did not show the high level of platelet activation normally associated with this level of adhesion. Thus the triphenylphosphonium polymer provides a material which allows platelet adhesion without concomitant activation. The results of the tests are as follows:

|   | Uncoated Plt. adhesion | Uncoated Plt. activation | Coated Plt. adhesion | Coated Plt. activation |
| --- | --- | --- | --- | --- |
| Abs., 450 nm | 0.479 | 0.550 | 0.456 | 0.125 |

We claim:

1. A surface having pendant zwitterionic groups each of which comprises an atom carrying an anionic charge and an atom carrying a cationic charge wherein said atom carrying a cationic charge has at least one monofunctional substituent which is selected from the group consisting of aryl, heteroaryl and aralkyl groups.

2. A surface according to claim 1 in which the zwitterionic groups have the formula I:

—YWZ in which one of Y and Z comprises the said atom carrying a cationic charge and the other of Y and Z comprises the said atom carrying an anionic charge; and W is selected from the group consisting of alkylene (including cycloalkylene and cycloalkyl alkylene), arylene, heteroarylene and alkarylene groups, in which any alkylene chain, including cycloalkylene, may be interrupted by one or more oxygen atoms, and any of which groups may be unsubstituted or substituted by nonionic non-interfering substituents.

3. A surface according to claim 2 in which Z comprises the atom carrying a cationic charge.

4. A surface according to claim 2 in which the zwitterionic group has the formula II:

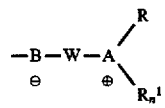

in which

B is a divalent anionic moiety;

W is as defined in claim 2;

A is the said atom carrying a cationic charge and is selected from the group consisting of a nitrogen atom, a phosphorus atom and a sulphur atom;

n is 1 when A is sulphur and n is 2 when A is nitrogen or phosphorus;

R is selected from the group consisting of aryl, heteroaryl and alkaryl groups; and the or each R$^1$ is independently selected from aryl, heteroaryl, aralkyl and alkyl groups and hydrogen atoms.

5. A surface according to claim 4 wherein R is an aryl group.

6. A surface according to claim 5 wherein R is phenyl.

7. A surface according to claim 4 in which each R$^1$ is aryl.

8. A surface according to claim 7 in which each R$^1$ is phenyl.

9. A surface according to claim 4 wherein the group W comprises a C$_{5-10}$ alkylene group separating the anionic and cationic atoms.

10. A surface according to claim 4 in which the group B is

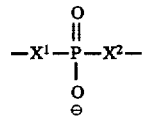

in which X$^1$ and X$^2$ are independently selected from a bond, —O—, —NH— and —S—.

11. A surface according to claim 2 in which the group —YWZ is part of a compound of the formula VI:

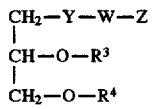

in which R$^3$ and R$^4$ represent the same or different C$_{1-24}$ alkyl or alkanoyl groups, and Y, W and Z are as defined in claim 2.

12. A surface according to claim 2 in which the zwitterionic group is part of a compound of the formula VIII:

$$R^8-\underset{\underset{R^8}{|}}{\overset{\overset{R^5}{|}}{C}}-CH_2-Y-W-Z \qquad \text{VIII}$$

in which

Y, W and Z are as defined in claim 2;

$R^5$ is selected from the group consisting of hydrogen, polymerisable groups and $C_{1-12}$ alkyl groups, wherein the said alkyl groups are unsubstituted or substituted by a group capable of reacting with a hydroxyl, amino or carboxyl group, or with a biologically active compound;

each $R^8$ is the same and represents $R^9$—E—B'— where B' is —$CH_2$— or —C(=O)— and where E is selected from the group consisting of valence bonds and linking groups selected from —O—, —S—, —NH—, —OC(O)—, —C(O)—O—, —SC(O)—, —C(O)—S—, —NHC(O)—, —C(O)—NH—, —OC(O)O—, —SC(O)O—, —NHC(O)O—, —OC(O)S—, —SC(O)S—, —NHC(O)S—, —OC(O)NH—, —SC(O)NH— and —NHC(O)NH—, wherein $R^9$ is selected from the group consisting of hydrogen, alkyl, alkenyl and alkynyl groups of up to 25 carbon atoms, optionally containing one or more etheric oxygen atoms and unsubstituted or substituted by one or more fluorine atoms and/or functional groups capable of reacting to provide covalent attachment to a surface and/or polymerisable groups.

13. A surface according to claim 12 in which E is —O— and $R^9$ is selected from the group consisting of linear $C_{8-24}$-alkyl and -alkanoyl groups and B is —$CH_2$—.

14. A surface according to claim 12 wherein $R^5$ is a $C_{1-4}$ alkyl group.

15. A surface according to claim 2 in which the zwitterionic group is part of a polymer produced by polymerising a monomer of the formula IX:

$$CH_2=\underset{\underset{}{|}}{\overset{\overset{R^{10}}{|}}{C}}-\overset{\overset{O}{\|}}{C}-G-Y-W-Z \qquad \text{IX}$$

in which

Y, W and Z are as defined in claim 2;

$R^{10}$ is selected from the group consisting of hydrogen and $C_{1-4}$ alkyl; and G is selected from —O—$R^{12}$ and —N($R^{11}$)—$R^{12}$— wherein $R^{11}$ is selected from the group comprising hydrogen, $C_{1-4}$ alkyl and $R^{12}$—Y—W—Z, wherein $R^{12}$ is $C_{1-12}$ alkylene.

16. A surface according to claim 15 wherein $R^{10}$ is methyl.

17. A surface according to claim 15 wherein $R^{12}$ is $C_{2-6}$ alkylene.

18. A surface according to claim 15 in which the polymer is a copolymer of the monomer of the formula IX and a copolymerisable $C_{8-24}$-alkyl(alk) acrylate.

19. A compound of the formula X:

$$R^2-X^1-\underset{\underset{O}{\overset{\|}{\ominus}}}{\overset{\overset{O}{\|}}{P}}-X^2-W-A\underset{R^1{}_n}{\overset{\oplus}{\diagdown}}{\diagup}^R \qquad \text{X}$$

in which

W is a $C_{5-10}$ alkylene group;

A is selected from the group consisting of a nitrogen atom, a phosphorus atom and a sulphur atom;

n is 1 when A is sulphur and n is 2 when A is nitrogen or phosphorus;

R is selected from the group consisting of aryl, heteroaryl and alkaryl groups;

each $R^1$ is independently selected from aryl, heteroaryl aralkyl and alkyl groups and hydrogen atoms;

$X^1$ and $X^2$ are independently selected from a bond, —O—, —NH— and —S—; and $R^2$ is a group $$R^8-\underset{\underset{R^8}{|}}{\overset{\overset{R^5}{|}}{C}}-CH_2- \qquad \text{VIII}$$

in which $R^5$ is selected from the group consisting of hydrogen, polymerizable groups and $C_{1-12}$ alkyl groups, wherein said alkyl groups are unsubstituted or substituted by a group capable of reacting with a hydroxyl, amino or carboxyl group, or with a biologically active compound;

each $R^8$ is the same and represents —$R^9$—E—B'— where E is selected from the group consisting of valence bonds and linking groups selected from —O—, —S—, —NH—, —OC(O)—, —C(O)—O—, —SC(O)—, —C(O)—S—, —NHC(O)—, —C(O)—NH—, —OC(O)O—, —SC(O)O—, —NHC(O)O—, —OC(O)S—, —SC(O)S—, —NHC(O)S—, —OC(O)NH—, —SC(O)NH— and —NHC(O)NH—, where B' is —$CH_2$— or —C(=O)—, wherein $R^9$ is selected from the group consisting of hydrogen, alkyl, alkenyl and alkynyl groups of up to 25 carbon atoms, optionally containing one or more etheric oxygen atoms and unsubstituted or substituted by one or more fluorine atoms and/or functional groups capable of reacting to provide covalent attachment to a surface and/or polymerizable groups.

20. A compound according to claim 19 wherein R is an aryl group.

21. A compound according to claim 20 wherein R is phenyl.

22. A compound according to claim 19 in which E is —O— and $R^9$ is selected from the group comprising linear $C_{8-24}$-alkyl and -alkanoyl groups and B is —$CH_2$—.

23. A compound according to claim 19 wherein $R^5$ is a $C_{1-4}$ alkyl group.

24. A monomer of the formula IX:

$$CH_2=\underset{\underset{}{|}}{\overset{\overset{R^{10}}{|}}{C}}-\overset{\overset{O}{\|}}{C}-G-Y-W-Z$$

in which $R^{10}$ is selected from the group consisting of hydrogen and $C_{1-4}$ alkyl;

G is selected from —O—$R^{12}$ and —N($R^{11}$)—$R^{12}$—, wherein $R^{11}$ is selected from the group comprising hydrogen, $C_{1-4}$ alkyl and $R^{12}$—Y—W—Z, wherein $R^{12}$ is $C_{1-12}$ alkylene; and —YWZ is a zwitterionic group wherein W is selected from the group consisting of alkylene (including cycloalkylene and cycloalkyl alkylene), arylene, heteroarylene and alkarylene groups, in which any alkylene chain, including cycloalkylene, may be interrupted by one or more oxygen atoms, and any of which groups may be unsubstituted or substituted by nonionic non-interfering substituents; and one of Y and Z comprises an atom carrying a cationic charge and the other of Y and Z comprises an atom carrying an anionic charge.

25. A monomer according to claim 20 wherein $R^{10}$ is methyl.

26. A monomer according to claim 20 wherein $R^{12}$ is $C_{2-6}$ alkylene.

27. A monomer according to claim 20 wherein the group W comprises a $C_{5-10}$ alkylene group.

28. A monomer according to claim 20 wherein the zwitterionic group —YWZ has the formula II:

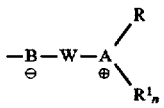
II in which

B is a divalent anionic moiety;

W is as defined in claim 20;

A is an atom carrying a cationic charge and is selected from the group consisting of a nitrogen atom, a phosphorus atom and a sulphur atom;

n is 1 when A is sulphur and n is 2 when A is nitrogen or phosphorus;

R is selected from the group consisting of aryl, heteroaryl and alkaryl groups; and the or each $R^1$ is independently selected from aryl, heteroaryl, aralkyl and alkyl groups and hydrogen atoms.

29. A polymer formed by polymerising a monomer according to claim 20.

30. A polymer according to claim 29 in which the monomer is copolymerized with a copolymerisable $C_{8-24}$-alkyl (alk)acrylate.

31. A polymer according to claim 30 in which the monomer is copolymerized with a $C_{12-18}$ linear alkyl methacrylate comonomer.

32. A process whereby a compound of the formula X:

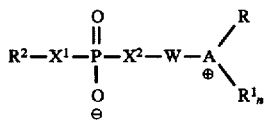
X in which

W is selected from the group consisting of alkylene (including cycloalkylene and cycloalkyl alkylene), arylene, heteroarylene and alkarylene groups, in which any alkylene chain, including cycloalkylene, may be interrupted by one or more oxygen atoms, and any of which groups may be unsubstituted or substituted by nonionic non-interfering substituents;

A is selected from the group consisting of a nitrogen atom, a phosphorus atom and a sulphur atom;

n is 1 when A is sulphur and n is 2 when A is nitrogen or phosphorus;

R is selected from the group consisting of aryl, heteroaryl and alkaryl groups;

the or each $R^1$ is independently selected from aryl, heteroaryl, aralkyl and alkyl groups and hydrogen atoms;

$X^1$ and $X^2$ are independently selected from a bond, —O—, —NH— and —S—; and $R^2$ is a group

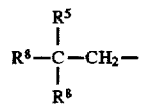
VIII in which $R^5$ is a $C_{1-4}$ alkyl group;

each $R^8$ is the same and represents $R^9$—E—B'— where E is —O— and $R^9$ is selected from the group comprising linear $C_{8-24}$-alkyl and -alkanoyl group, and B' is —$CH_2$—, in the form of a solution in an organic solvent is used to coat a substrate surface.

33. A process whereby a polymer made from a monomer of the formula IX:

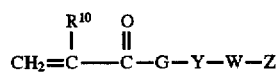
IX in which $R^{10}$ is selected from the group consisting of hydrogen and $C_{1-4}$ alkyl;

G is selected from —O—$R^{12}$ and —N($R^{11}$)—$R^{12}$—, wherein $R^{11}$ is selected from the group comprising hydrogen, $C_{1-4}$ alkyl and $R^{12}$—Y—W—Z, wherein $R^{12}$ is $C_{1-12}$ alkylene;

W is selected from the group consisting of alkylene (including cycloalkylene and cycloalkyl alkylene), arylene, heteroarylene and alkarylene groups, in which any alkylene chain, including cycloalkylene, may be interrupted by one or more oxygen atoms, and any of which groups may be unsubstituted or substituted by nonionic non-interfering substituents; and one of Y and Z comprises an atom carrying a cationic charge and the other of Y and Z comprises an atom carrying an anionic charge, in the form of a solution in a solvent is used to coat a substrate surface.

34. A process according to claim 32 wherein the obtained coating improves the haemocompatability of the surface.

35. A process according to claim 33 wherein the obtained coating improves the haemocompatability of the surface.

36. A process according to claim 32 whereby the adhesion of platelets to the coated substrate is substantially unaffected by the coating.

37. A process according to claim 33 whereby the adhesion of platelets to the coated substrate is substantially unaffected by the coating.

38. A blood contacting device having a blood contacting surface which is a surface according to claim 1.

39. A device according to claim 34 which is an implantable prosthesis.

* * * * *